(12) United States Patent
Paul et al.

(10) Patent No.: US 12,195,715 B2
(45) Date of Patent: Jan. 14, 2025

(54) PERFUSION BIOPROCESSING SYSTEM AND METHOD OF OPERATING THE SAME

(71) Applicant: Cytiva Sweden AB, Uppsala (SE)

(72) Inventors: Praveen Paul, Karnataka (IN); Prashanth Hosabettu Mohan, Karnataka (IN); Ajay Gore, Karnataka (IN); Sahebagouda Alagur, Karnataka (IN)

(73) Assignee: Cytiva Sweden AB, Uppsala (SE)

( * ) Notice: Subject to any disclaimer, the term of this patent is extended or adjusted under 35 U.S.C. 154(b) by 831 days.

(21) Appl. No.: 17/277,094

(22) PCT Filed: Sep. 20, 2019

(86) PCT No.: PCT/EP2019/075411
§ 371 (c)(1),
(2) Date: Mar. 17, 2021

(87) PCT Pub. No.: WO2020/058509
PCT Pub. Date: Mar. 26, 2020

(65) Prior Publication Data
US 2021/0395664 A1 Dec. 23, 2021

(30) Foreign Application Priority Data
Sep. 21, 2018 (IN) .............................. 201841035642

(51) Int. Cl.
*B01D 61/12* (2006.01)
*B01D 61/22* (2006.01)
(Continued)

(52) U.S. Cl.
CPC ............. *C12M 29/04* (2013.01); *B01D 61/12* (2013.01); *B01D 61/22* (2013.01); *C12M 29/10* (2013.01);
(Continued)

(58) Field of Classification Search
CPC ...... C12M 29/04; C12M 29/10; C12M 29/16; C12M 29/18; C12M 33/14; C12M 41/40;
(Continued)

(56) References Cited

U.S. PATENT DOCUMENTS 9,765,363 B1 * 9/2017 Renninger ............. C12M 41/18
2002/0043487 A1 4/2002 Schick
(Continued)

FOREIGN PATENT DOCUMENTS

| CN | 101516477 A | 8/2009 |
| CN | 101879387 A | 11/2010 |

(Continued)

OTHER PUBLICATIONS

Office Action Issued in Chinese Patent Application No. 201980061672.4, mailed Sep. 15, 2022 with English Translation. (27 pages).
(Continued)

*Primary Examiner* — Joseph W Drodge
(74) *Attorney, Agent, or Firm* — Eversheds-Sutherland (US) LLP (57) ABSTRACT

A perfusion bioprocessing system (10) includes a bioreactor (12) and a recirculation flow path (14) provided with at least in one first feed flow control device (46) and at least one second feed control device (48). The perfusion bioprocessing system (10) further includes a first tangential flow filter (16) coupled to the bioreactor (12) via the recirculation flow path (14) and a second tangential flow filter (18) coupled to the bioreactor (12) via the recirculation flow path (14). The first tangential flow filter and the second tangential flow filter are coupled to a permeate flow path and a retentate flow path. Additionally, the perfusion bioprocessing system (10) includes a control unit (90) coupled to the at least one first feed flow control device (38) and the at least one second feed control device (40).

24 Claims, 2 Drawing Sheets (51) Int. Cl.
  *C12M 1/00* (2006.01)
  *C12M 1/34* (2006.01)
(52) U.S. Cl.
  CPC ............ *C12M 41/40* (2013.01); *C12M 41/44* (2013.01); *C12M 47/10* (2013.01); *B01D 2311/253* (2022.08); *B01D 2311/2688* (2013.01); *B01D 2315/10* (2013.01); *B01D 2317/04* (2013.01); *C02F 2209/00* (2013.01); *C02F 2209/001* (2013.01); *C02F 2209/005* (2013.01); *C02F 2209/40* (2013.01)
(58) Field of Classification Search
  CPC ....... C12M 41/44; C12M 47/10; B01D 61/12; B01D 61/14; B01D 61/145; B01D 61/147; B01D 61/1471; B01D 61/20; B01D 61/22; B01D 61/58; B01D 2315/14; B01D 2315/18; B01D 2311/253; B01D 2311/2688; B01D 2315/10; B01D 2317/04; C02F 1/008; C02F 1/44; C02F 1/444; C02F 2209/00; C02F 2209/001; C02F 2209/005; C02F 2209/03; C02F 2209/40
  See application file for complete search history.

(56) References Cited

U.S. PATENT DOCUMENTS

| | | | |
|---|---|---|---|
| 2005/0029192 A1* | 2/2005 | Arnold | B01D 61/025 210/652 |
| 2006/0027500 A1 | 2/2006 | Schick | |
| 2015/0360180 A1* | 12/2015 | Lutz | B01D 65/02 210/636 |
| 2016/0059159 A1* | 3/2016 | Steen | B01D 63/0822 210/788 |
| 2016/0144320 A1 | 5/2016 | Nishio et al. | |
| 2016/0176740 A1 | 6/2016 | Honda et al. | |
| 2016/0222337 A1* | 8/2016 | Serway | C12M 29/10 |
| 2016/0237944 A1* | 8/2016 | Adelman | F02D 41/3082 |
| 2017/0173537 A1* | 6/2017 | Gagnon | B01D 61/146 |
| 2022/0073861 A1* | 3/2022 | Lu | C12M 41/40 |

FOREIGN PATENT DOCUMENTS

| | | |
|---|---|---|
| CN | 104220149 A | 12/2014 |
| CN | 204637683 U | 9/2015 |
| CN | 105722967 A | 6/2016 |
| CN | 205527878 U | 8/2016 |
| CN | 108434990 A | 8/2018 |
| EP | 1782874 A1 | 5/2007 |
| EP | 2308586 A1 | 4/2011 |
| JP | S6019004 A | 1/1985 |
| JP | S62191097 A | 8/1987 |
| JP | H0724265 A | 1/1995 |
| JP | H11169851 A | 6/1999 |
| JP | 2000237502 A | 9/2000 |
| JP | 2001029756 A | 2/2001 |
| JP | 2010051927 A | 3/2010 |
| JP | 2013188710 A | 9/2013 |
| JP | 2013223866 A | 10/2013 |
| JP | 2017131886 A | 8/2017 |
| WO | 0048703 A1 | 8/2000 |
| WO | 2013031237 A1 | 3/2013 |
| WO | 2014204002 A1 | 12/2014 |
| WO | 2017/143197 A1 | 8/2017 |
| WO | WO-2018222550 A1 * | 12/2018 ............. B01D 61/18 |

OTHER PUBLICATIONS

Chinese Office Action for CN Application No. 201980061672.4, dated Jan. 16, 2023 (30 pages, with English translation).
Peng, J., et al. "Insect Cell Biotechnology", Huazhong Normal University Press, 2010, pp. 296-297.
Chinese Search Report for CN Application No. 201980061672.4, dated Apr. 19, 2023 (2 pages, with English translation).
"Biochemical Separation Engineering", Yan Xikang, pp. 84-85, Chemical Industry Press, Feb. 2001.
"Industrial Water Treatment", Zhu Yuehai et al, p. 402, Tongji University Press, Sep. 2016.
Chinese Office Action for CN Application No. 201980061672.4, dated Jun. 6, 2023 (14 pages, with English translation).
Japanese Office Action for JP Application No. 2021-515580, dated Sep. 4, 2023 (13 pages, with English translation).
PCT International Search Report and Written Opinion for PCT/EP2019/075411 mailed Jan. 10, 2020 (9 pages).
Office Action issued in Japanese application No. 2021-515580, mailed Jul. 1, 2024 (20 pages).

* cited by examiner

FIG. 1

PERFUSION BIOPROCESSING SYSTEM AND METHOD OF OPERATING THE SAME

CROSS REFERENCE TO RELATED APPLICATIONS

This application claims the priority benefit of PCT/EP2019/075411, filed on Sep. 20, 2019, which claims the benefit of Indian Application No. 201841035642, filed on Sep. 21, 2018, the entire contents of which are incorporated by reference herein.

FIELD OF INVENTION

The embodiments of the present specification relate generally to filtration systems, and more particularly, to a perfusion bioprocessing system having a plurality of tangential flow filters and a method for operating the perfusion bioprocessing system.

BACKGROUND OF INVENTION

Existence of many substances as solutions or mixtures created a need for processes to be developed to separate the solutions or mixtures. The need to purify, recover, isolate, and remove substances in process streams in chemical, pharmaceutical, food, petroleum, healthcare, and waste water applications has driven the need for separation technology.

The most common filtration processes are microfiltration (MF), ultrafiltration (UF), and reverse osmosis (RO). Such filtration processes are pressure driven and are used for separation of macromolecules from a fluid using a filter. The filter serves as a selective barrier by permitting certain constituents of a mixture to passthrough while retaining other constituents of the mixture. The filtration process results in two phases, permeate and retentate phases.

For a bioprocessing application, continuous processing is a growing trend because a smaller bioreactor can be used to produce a required quantity of a product compared to use of a larger bioreactor operated in batch and fed batch mode. Perfusion enables continuous processing by enabling continuous nutrient supply and removal of spent media and metabolic wastes. The continuous process results in better product yield, product quality, process intensification, reduced capex, and reduced operation expenditure.

A drawback associated with use of filter separation process is a phenomenon known as fouling of the filter. Fouling is the deposition of material, referred to as foulant, on a surface of the membrane or pores of the filter, leading to a change in filter performance or even complete plugging of the filter and increase in product retention resulting in loss of process and product quality. Filter clogging may arise due to various reasons such as presence of cells, cell debris, extracellular components in the process fluid and addition of certain materials such as an antifoam agent required for the process. As a result, filter efficiency reduces due to the filter clogging, which in turn impacts filtration quality, loss of control of continuous process, and increases the overall processing time. In scenarios where the tangential flow filter is used for continuous processing, filter clogging restricts a duration for which the process can be run without interruption. Specifically, filter clogging restricts a duration of perfusion and limits a cell density that can be achieved at the end of the process. Also, the tangential flow filter would need to be manually changed leading to stoppage of the process for filter replacement.

There is a need for an enhanced perfusion bioprocessing system and a method for operating the perfusion bioprocessing system.

BRIEF DESCRIPTION OF INVENTION

In accordance with one aspect of the present specification, a method for operating a perfusion bioprocessing system is disclosed. The method includes step of inducing a first quantity of a process fluid to flow from a bioreactor to a first tangential flow filter via a recirculation flow path. The method further includes step of operating a control unit to control at least one first feed flow control device in the recirculation flow path for controlling the flow of the first quantity of the process fluid. Furthermore, the method includes step of allowing the first tangential flow filter to separate the first quantity of the process fluid into a first quantity of a permeate fluid and a first quantity of a retentate fluid. The method also includes step of inducing a second quantity of the process fluid to flow from the bioreactor to a second tangential flow filter via the recirculation flow path, bypassing the first tangential flow filter, upon determination of a clogged or a substantially clogged condition of the first tangential flow filter by the control unit. Additionally, the method includes step of operating the control unit to control at least one of the at least one first feed flow control device and at least one second feed control device in the recirculation flow path for controlling the flow of the second quantity of the process fluid. Further, the method includes step of allowing the second tangential flow filter to separate the second quantity of the process fluid into a second quantity of the permeate fluid and a second quantity of the retentate fluid.

In accordance with another aspect of the present specification, a perfusion bioprocessing system is disclosed. The perfusion bioprocessing system includes a bioreactor and a recirculation flow path provided with at least one first feed flow control device and at least one second feed control device. The perfusion bioprocessing system further includes a first tangential flow filter coupled to the bioreactor via the recirculation flow path and a second tangential flow filter coupled to the bioreactor via the recirculation flow path. Furthermore, the perfusion bioprocessing system includes a permeate flow path coupled to the first tangential flow filter and the second tangential flow filter and a retentate flow path coupled to the first tangential flow filter and the second tangential flow filter. Additionally, the perfusion bioprocessing system includes a control unit coupled to the at least one first feed flow control device and the at least one second feed control device. The control unit is configured to control the at least one first feed flow control device for controlling a flow of a first quantity of a process fluid from the bioreactor to the first tangential flow filter via the recirculation flow path. The control unit is further configured to control at least one of the at least one first feed flow control device and the at least one second feed control device for controlling a flow of a second quantity of the process fluid from the bioreactor to the second tangential flow filter via the recirculation flow path, bypassing the first tangential flow filter upon determination of a clogged condition or a substantially clogged condition of the first tangential flow filter.

BRIEF DESCRIPTION OF DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Unless defined otherwise, technical and scientific terms used herein have the same meaning as is commonly understood by one of ordinary skill in the art to which this disclosure belongs. The terms "first," "second," and the like, as used herein do not denote any order, quantity, or importance, but rather are used to distinguish one element from another. Also, the terms "a" and "an" do not denote a limitation of quantity, but rather denote the presence of at least one of the referenced items. The use of "including", "comprising", or "having" and variations thereof herein are meant to encompass the items listed thereafter and equivalents thereof as well as additional items.

In accordance with an embodiment of the present specification, a method for operating a perfusion bioprocessing system is disclosed. The method includes inducing a first quantity of a process fluid to flow from a bioreactor to a first tangential flow filter via a recirculation flow path. The method further includes operating a control unit to control at least one first feed flow control device in the recirculation flow path for controlling the flow of the first quantity of the process fluid. Furthermore, the method includes allowing the first tangential flow filter to separate the first quantity of the process fluid into a first quantity of a permeate fluid and a first quantity of a retentate fluid. The method further includes inducing a second quantity of the process fluid to flow from the bioreactor to a second tangential flow filter via the recirculation flow path, bypassing the first tangential flow filter, upon determination of a clogged or a substantially clogged condition of the first tangential flow filter by the control unit. Additionally, the method includes operating the control unit to control at least one of the at least one first feed flow control device and at least one second feed control device in the recirculation flow path for controlling the flow of the second quantity of the process fluid. Furthermore, the method includes allowing the second tangential flow filter to separate the second quantity of the process fluid into a second quantity of the permeate fluid and a second quantity of the retentate fluid.

In accordance with another embodiment, an associated system is disclosed. In accordance with the embodiments of the present specification, the exemplary system and method enable to switch the flow of the process fluid between the plurality of tangential flow filters upon determination of a clogged or a substantially clogged condition of the first tangential flow filter by the control unit. The switching of the flow of the process fluid between the tangential flow filters is completely sterile and automatic since there is no requirement for an intervention of a user. Furthermore, there is no need to manually replace the tangential flow filters depending on the process requirement. Hence, there is no need to stop the process for changing the tangential flow filters which is undesirable for a perfusion process, for example.

Figure 1:
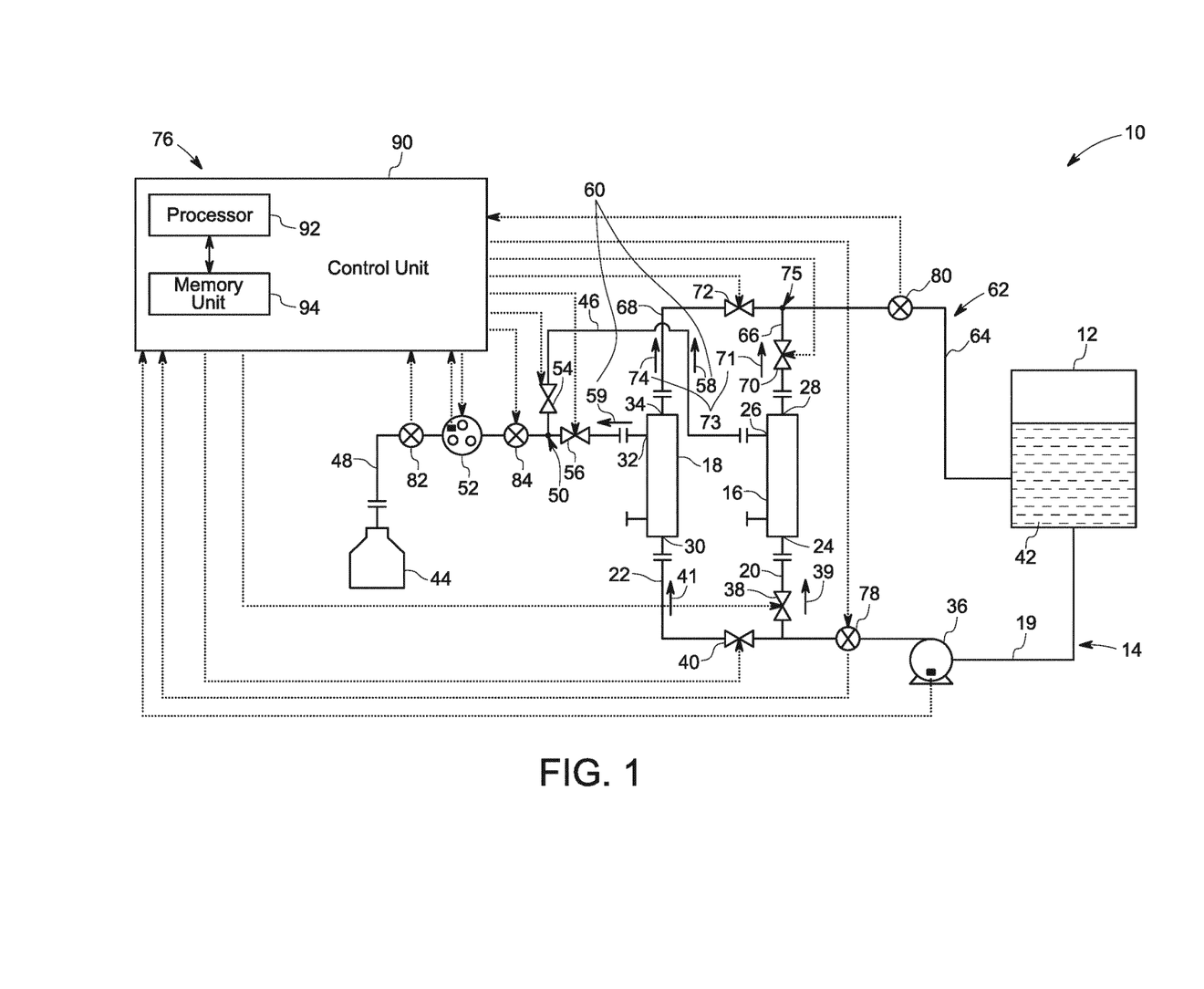
FIG. 1 is a schematic diagram of a perfusion bioprocessing system having a plurality of tangential flow filters in accordance with an embodiment of the present specification.

Referring to FIG. 1, a schematic diagram of a perfusion bioprocessing system 10 in accordance with an embodiment of the present specification is shown. In the illustrated embodiment, the perfusion bioprocessing system 10 includes a bioreactor 12 coupled via a recirculation flow path 14 to a first tangential flow filter 16 and a second tangential flow filter 18. In one embodiment, the first and second tangential flow filters 16, 18 may be hollow fiber filters. The recirculation flow path 14 has a main portion 19 and first and second branch portions 20, 22 extending from the main portion 19. In the illustrated embodiment, the first and second branch portions 20 22 extend parallel to each other. The first tangential flow filter 16 has an inlet 24, a first outlet 26, and a second outlet 28. The second tangential flow filter 18 has an inlet 30, a first outlet 32, and a second outlet 34. Specifically, the first branch portion 20 is coupled to the inlet 24 of the first tangential flow filter 16. The second branch portion 22 is coupled to the inlet 30 of the second tangential flow filter 18.

The perfusion bioprocessing system 10 further includes a recirculation pump 36, a first feed flow control device 38, and a second feed flow control device 40 coupled to the recirculation flow path 14. In the illustrated embodiment, the first and second feed flow control devices 38, 40 are referred to herein as first and second feed flow control valves. Specifically, the first feed flow control valve 38 is coupled to the first branch portion 20 and disposed downstream of the recirculation pump 36 and upstream of the first tangential flow filter 16. The second feed flow control valve 40 is coupled to the main portion 19 and disposed downstream of the recirculation pump 36 and upstream of the second tangential flow filter 18. The bioreactor 12 is used for storage of a process fluid 42 associated with cell culture, for example. Specifically, the recirculation pump 36 is used for feeding the process fluid 42 at a predetermined flow rate from the bioreactor 12 to the first tangential flow filter 16 or the second tangential flow filter 18 via the recirculation flow path 14. The first and second feed flow control valves 38, 40 are used for controlling a flow of the process fluid 42 via the recirculation flow path 14 to the first tangential flow filter 16 or the second tangential flow filter 18. If the first feed flow control valve 38 is opened and the second feed flow control valve 40 is closed, a first quantity 39 of the process fluid 42 is routed through the first tangential flow filter 16. If the first feed flow control valve 38 is closed and the second feed flow control valve 40 is opened, a second quantity of 41 of the process fluid 42 is routed through the second tangential flow filter 18.

Additionally, the perfusion bioprocessing system 10 includes a permeate collection unit 44 coupled to the first outlet 26 of the first tangential flow filter 16 via a first permeate flow path 46 and a second permeate flow path 48. The first permeate flow path 46 and the second permeate flow path 48 may also be collectively referred to as a permeate flow path. Further, the permeate collection unit 44 is coupled to the first outlet 32 of the second tangential flow filter 18 via the second permeate flow path 48. The first permeate flow path 46 is coupled to the second permeate flow path 48, at a location 50 downstream of the second tangential flow filter 18. The perfusion bioprocessing system 10 also includes a permeate pump 52 coupled to the second permeate flow path 48. Also, the perfusion bioprocessing system 10 includes a first permeate flow control device 54 coupled to the first permeate flow path 46 and a second permeate flow control device 56 coupled to the second permeate flow path 48. The first and second permeate flow control devices 54, 56 are referred to herein as first and second permeate flow control valves. The second permeate flow control valve 56 is disposed upstream of the location 50. The first tangential flow filter 16 is used for separating a first quantity 58 of a permeate fluid 60 from the first quantity 39 of the process fluid 42 by utilizing a pressure difference across the first tangential flow filter 16. If the first permeate flow control valve 54 is opened and the second permeate flow control valve 56 is closed, the permeate pump 52 can be operated to feed the first quantity 58 of the permeate fluid 60 at a predetermined flow rate to the permeate collection unit 44 via the first permeate flow path 46 and the second permeate flow path 48. If the first permeate flow control valve 54 is closed and the second permeate flow control valve 56 is opened, the permeate pump 52 can be operated to feed a second quantity 59 of the permeate fluid 60 at a predetermined flow rate to the permeate collection unit 44 via the second permeate flow path 48.

Further, the bioreactor 12 is coupled to the second outlet 28 of the first tangential flow filter 16 and the second outlet 34 of the second tangential flow filter 18 via a retentate flow path 62. Specifically, the retentate flow path 62 has a main portion 64, a first branch portion 66, and a second branch portion 68. The second outlet 28 of first tangential flow filter 16 is coupled via the first branch portion 66 and the main portion 64 to the bioreactor 12. Similarly, the second outlet 34 of the second tangential flow filter 18 is coupled via the second branch portion 68 and the main portion 64 to the bioreactor 12. A first retentate flow control device 70 is coupled to the first branch portion 66 and a second retentate flow control device 72 is coupled to the main portion 64. The first and second retentate flow control devices 70, 72 are referred to herein as first and second retentate flow control valves. Specifically, the second retentate flow control valve 72 is disposed downstream of the second branch portion 68 and upstream of a location 75 at which the first branch portion 66 is connected to the main portion 64. If the first retentate flow control valve 70 is opened and the second retentate flow control valve 72 is closed, a first quantity 71 of a retentate fluid 73 flows via the second outlet 28 of the first tangential flow filter 16, the first branch portion 66, and the main portion 64 to the bioreactor 12. The first quantity 71 of the retentate fluid 73 is a remaining portion of the first quantity 39 of the process fluid 42 after separation of the first quantity 58 of the permeate fluid 60. If the first retentate flow control valve 70 is closed and the second retentate flow control valve 72 is opened, a second quantity 74 of the retentate fluid 73 flows via the second outlet 34 of the second tangential flow filter 18, the second branch portion 68, and the main portion 64 to the bioreactor 12. The second quantity 74 of the retentate fluid 73 is a remaining portion of the second quantity of 41 of the process fluid 42 after separation of the second quantity 59 of the permeate fluid 60. It should be noted herein that the illustrated perfusion bioprocessing system 10 is an exemplary embodiment and should not be construed as a limitation. The configuration of the perfusion bioprocessing system 10 may vary depending upon the application. In other embodiments, the number of tangential flow filters, valves, and pumps may vary depending on the application and process requirements.

In another embodiment, instead of using the recirculation pump 36, a pressurized gas may be fed from a gas source (not shown) to the bioreactor 12 via a filter (not show) for feeding the process fluid 42 from the bioreactor 12 to the first and second tangential flow filters 16, 18 via the recirculation flow path 14. In such an embodiment, the permeate pump 52 may not be required.

In the illustrated embodiment, the perfusion bioprocessing system 10 further includes a control system 76 having a feed pressure sensor 78 coupled to the recirculation flow path 14. Specifically, the feed pressure sensor 78 is coupled to the main portion 19 of the recirculation flow path 14. The feed pressure sensor 78 is located downstream of the recirculation pump 36 and upstream of the first and second branch portions 20, 22. The feed pressure sensor 78 is used to sense a pressure of the process fluid 42 flowing through the main portion 19 of the recirculation flow path 14. The control system 76 additionally includes a retentate pressure sensor 80 coupled to the main portion 64 of the retentate flow path 62. Specifically, the retentate pressure sensor 80 is disposed downstream of the first and second branch portions 66, 68 of the retentate flow path 62. The retentate pressure sensor 80 is used to sense a pressure of the retentate fluid 73 flowing through the main portion 64 of the retentate flow path 62.

Additionally, the control system 76 includes a permeate flow sensor 82 and a permeate pressure sensor 84 coupled to the second permeate flow path 48. The permeate flow sensor 82 is located downstream of the permeate pump 52. The permeate flow sensor 82 is used to measure a flow rate of the permeate fluid 60 flowing through the second permeate flow path 48. In one embodiment, the permeate flow sensor 82 may output a signal representative of the flow rate of the permeate fluid 60 flowing through the second permeate flow path 60. In another embodiment, the permeate flow senor 82 may output a signal representative of a parameter, for example, volume or velocity, of the permeate fluid 60 for computing the flow rate of the permeate fluid 60. Any type of flow sensor which may be used for measuring the flow rate of the permeate fluid 60 is envisioned. The permeate pressure sensor 84 is located upstream of the permeate pump 52 and downstream of the location 50. The permeate pressure sensor 84 is used to sense a pressure of the permeate fluid 60 flowing through the second permeate flow path 48.

Furthermore, the control system 76 includes a revolution per minute (rpm) sensor 86 coupled to the feed pump 36 and another rpm sensor 88 coupled to the permeate pump 52. The rpm sensor 86 is used to measure a rpm of the feed pump 36. The rpm sensor 88 is used to measure a rpm of the permeate pump 52.

Further, in the illustrated embodiment, the control system 76 includes a control unit 90 having a processor 92 and a memory unit 94 coupled to the processor 92. In some embodiments, the control unit 90 is used to control at least one function of the perfusion bioprocessing system 10. In certain embodiments, the control unit 90 may include more than one processor co-operatively working with each other for performing intended functionalities. The control unit 90 is further configured to store and retrieve contents into and from the memory unit 94. In one embodiment, the control unit 90 is configured to initiate and control the functionality of the perfusion bioprocessing system 10.

In one embodiment, the control unit 90 includes at least one of a general-purpose computer, a graphics processing unit (GPU), a digital signal processor, and a controller. In other embodiments, the control unit 90 includes a customized processor element such as, but not limited to, an application-specific integrated circuit (ASIC) and a field-programmable gate array (FPGA). In some embodiments, the control unit 90 may be communicatively coupled with at least one of a keyboard, a mouse, and any other input device and configured to receive commands and/or parameters from an operator via a console.

In one embodiment, the memory unit 94 is a random-access memory (RAM), a read only memory (ROM), a flash memory, or any other type of computer readable memory accessible by the processor 92. Also, in certain embodiments, the memory unit 94 may be a non-transitory computer readable medium encoded with a program having a plurality of instructions to instruct the processor 92 to perform a sequence of steps to operate perfusion bioprocessing system 10.

In the illustrated embodiment, the control unit 90 is communicatively coupled to the permeate flow sensor 82. In one embodiment, the control unit 90 is configured to receive the output signal representative of the flow rate of the permeate fluid 60 from the permeate flow sensor 82. In another embodiment, the control unit 90 is configured to receive the output signal representative of a parameter, for example, volume or velocity, of the permeate fluid 60 from the permeate flow sensor 82 for computing the flow rate of the permeate fluid 60 in accordance with a known technique.

The control unit 90 is also communicatively coupled to the rpm sensors 86, 88 and configured to receive output signals representative of rpms of the feed pump 36 and the permeate pump 52. The control unit 90 is further configured to determine a variation in rpms of the feed pump 36 and the permeate pump 52 based on the output signals from the rpm sensors 86, 88.

Additionally, the control unit 90 is communicatively coupled to the feed pressure sensor 78, the retentate pressure sensor 80, and the permeate pressure sensor 84. In one embodiment, the control unit 90 is communicatively coupled to the feed, retentate, and permeate pressure sensors 78, 80, 84 and configured to determine a Trans-Membrane Pressure (TMP) of the first tangential flow filter 16 based on outputs from the feed, retentate, and permeate pressure sensors 78, 80, 84. It should be noted herein that the TMP is representative of a pressure that is needed to pass fluid (water) through a filter. In another embodiment, the control unit 90 is configured to determine a pressure difference across the second tangential flow filter 16 based outputs from the feed and retentate pressure sensors 78, 80.

Furthermore, the control unit 90 is coupled to and configured to control operations of the first and second feed flow control valves 38, 40, the first and second permeate flow control valves 54, 56, and the first and second retentate flow control valves 70, 72. In one embodiment, the control unit 90 is configured to control the first feed flow control valve 38 for controlling a flow of the first quantity 39 of the process fluid 42 from the bioreactor 12 to the first tangential flow filter 16 via the main portion 19 and the first branch portion 20 of the recirculation flow path 14. Further, the control unit 90 is configured to control the first feed flow control valve 38 and the second feed flow control valve 40 for controlling a flow of the second quantity 41 of the process fluid 42 from the bioreactor 12 to the second tangential flow filter 18 via the main portion 19 and the second branch portion 22 of the recirculation flow path 14, bypassing the first tangential flow filter 16 upon determination of the clogged or the substantially clogged condition of the first tangential flow filter 16.

As noted earlier, the control unit 90 facilitates switching of the flow of the process fluid 42 between the first and second tangential flow filters 16, 18 automatically. Hence, there is no requirement for an intervention of a user. Furthermore, there is no need to manually replace the tangential flow filters depending on the process requirement.

Figure 2:
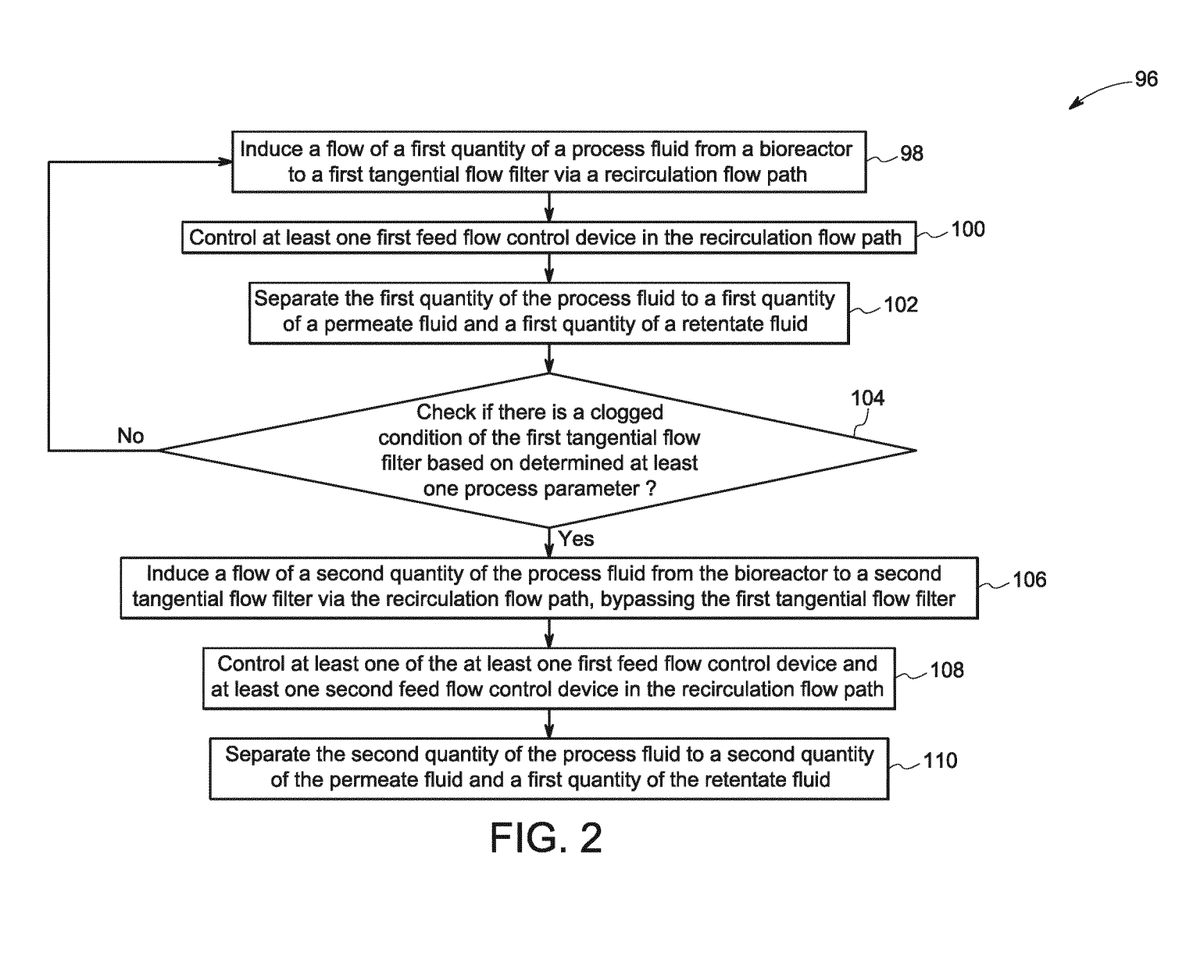
FIG. 2 is a flow chart illustrating a plurality of steps involved in a method for operating the perfusion bioprocessing system having the plurality of tangential flow filters in accordance with another embodiment of the present specification.

FIG. 2 is a flow chart illustrating a method 96 for operating the perfusion bioprocessing system 10 in accordance with the embodiment of FIG. 1. The method 96 includes inducing the flow of the first quantity 39 of the process fluid 42 from the bioreactor 12 to the first tangential flow filter 16 via the recirculation flow path 14 as represented by step 98. In one embodiment, the control unit 90 operates the recirculation pump 36, opens the first feed flow control valve 38, and closes the second feed flow control valve 40 to control the flow of the first quantity 39 of the process fluid 42 from the bioreactor 12 to the first tangential flow filter 16 via the main portion 19 and the first branch portion 20 of the recirculation flow path 14 as represented by step 100. In another embodiment, instead of using the recirculation pump 36, a pressurized gas may be fed from a gas source to the bioreactor 12 via a filter for feeding the first quantity 39 of the process fluid 42 from the bioreactor 12 to the first tangential flow filter 16 via the main portion 19 and the first branch portion 20 of the recirculation flow path 14. The first tangential flow filter 16 separates the first quantity 39 of the process fluid 42 into the first quantity 58 of the permeate fluid 60 and the first quantity 71 of the retentate fluid 73 as represented by the step 102. Specifically, the first quantity 39 of the process fluid 42 is passed tangentially across the first tangential flow filter 16 at a positive pressure relative to a permeate side of the first tangential flow filter 16. The control unit 90 operates the permeate pump 52, opens the first permeate flow control valve 54, and closes the second permeate flow control valve 56 to feed the first quantity 58 of the permeate fluid 60 to the permeate collection unit 44 via the first permeate flow path 46 and the second permeate flow path 48. Further, the control unit 90 opens the first retentate flow control valve 70 and closes the second retentate flow control valve 72 to feed the first quantity 71 of the retentate fluid 73 through the first branch portion 66 and the main portion 64 of the retentate flow path 62 to the bioreactor 12.

In accordance with the embodiment of the present specification, the control unit 90 is used determine the clogged or the substantially clogged condition of the first tangential flow filter 16 based on at least one process parameter discussed herein as represented by step 104. In one embodiment, the control unit 90 determines a permeate flux rate of the first tangential flow filter 16 based on the determined flow rate of the first quantity 58 of the permeate fluid 60 by the permeate flow sensor 82. It should be noted herein that the permeate flux rate of the first tangential flow filter 16 is defined as the measured flow rate of the first quantity 58 of the permeate fluid 60 per unit area of the first tangential flow filter 16. In one embodiment, the control unit 90 determines the clogged or the substantially clogged condition of the first tangential flow filter 16 if the determined permeate flux rate is less than a threshold permeate flux rate. In one example, the threshold permeate flux rate is 70%.

In another embodiment, the control unit 90 determines change in rpm, for example, an increase in rpm of the permeate pump 52 based on at least one of the flow rate of the first quantity 58 of the permeate fluid 60 and determined revolutions per minute of the permeate pump 52. Specifically, in such an embodiment, the control unit 90 determines the clogged or the substantially clogged condition of the first tangential flow filter 16 based on the determined permeate flux rate of the first tangential flow filter 16 and the change in rpm of the permeate pump 52. In one such specific embodiment, the control 90 determines the clogged condition or the substantially clogged condition of the first tangential flow filter 16 if the determined permeate flux rate is less than a threshold permeate flux rate and based on the change in rpm of the permeate pump 52.

In yet another embodiment, the control unit 90 determines the clogged or the substantially clogged condition of the first tangential flow filter 16 based on the determined pressure of the first quantity 58 of the permeate fluid 60 by the permeate pressure sensor 84. Specifically, the control unit 90 determines the clogged or the substantially clogged condition of the first tangential flow filter 16 if the determined pressure of the first quantity 58 of the permeate fluid 60 is less than a threshold pressure.

In yet another embodiment, the control unit 90 determines the clogged or the substantially clogged condition of the first tangential flow filter 16 based on the determined rpm of the recirculation pump 36 by the rpm sensor 86. In yet another embodiment, the control unit 90 determines the clogged or the substantially clogged condition of the first tangential flow filter 16 if the determined rpm of the recirculation pump 36 is greater than a threshold rpm.

In another embodiment, the control unit 90 determines the clogged condition or the substantially clogged of the first tangential flow filter 16 based on a pressure difference across the first tangential flow filter 16 based outputs from the feed and retentate pressure sensors 78, 80 84. Specifically, if the pressure difference across the first tangential flow filter 16 is greater than a threshold pressure, the control unit 66 determines clogging or substantial of the first tangential flow filter 16.

In yet another embodiment, the control unit 90 determines the clogged or the substantially clogged condition of the first tangential flow filter 16 based on the determined TMP of the first tangential flow filter 16 computed based on outputs from the feed, retentate, and permeate pressure sensors 78, 80, 84. TMP is calculated by the control unit 90 based on the following relation:

$$TMP=((p_2+p_3)/2)-p_1$$

where $p_1$ is an output of the permeate pressure sensor 84, $p_2$ is an output of the feed pressure sensor 78, $p_3$ is an output of the retentate pressure sensor 80. If the TMP is greater than a threshold pressure, the control unit 90 determines clogging or substantial clogging of the first tangential flow filter 16. In one embodiment, the control unit 90 determines the threshold pressure based on a plurality of parameters such as but not limited to the determined flow rate of the first quantity 58 of the permeate fluid 60 in the first permeate flow path 46, cell viability, cell density, and the determined permeate flux rate of the first tangential flow filter 16. In one specific embodiment, a ratio of the TMP to the threshold pressure is in a range of 1.5 to 2.

It should be noted herein that the threshold pressures/flow rates/rpm/flux discussed herein are set based on the predetermined process optimization values. If the clogged or the substantially clogged condition of the first tangential flow filter 16 is determined, the method 96 further includes inducing the flow of the second quantity 41 of the process fluid 42 from the bioreactor 12 to the second tangential flow filter 18 via the recirculation flow path 14, bypassing the first tangential flow filter 16 as represented by the step 106. In one embodiment, the control unit 90 operates the recirculation pump 36, closes the first feed flow control valve 38, and opens the second feed flow control valve 40 to control the flow of the second quantity 41 of the process fluid 42 from the bioreactor 12 to the second tangential flow filter 16 via the main portion 19 and the second branch portion 22 of the recirculation flow path 14 as represented by step 108. In another embodiment, instead of using the recirculation pump 36, a pressurized gas may be fed from the gas source to the bioreactor 12 via the filter for feeding the second quantity 41 of the process fluid 42 from the bioreactor 12 to the second tangential flow filter 16 via the main portion 19 and the second branch portion 20 of the recirculation flow path 14. The second tangential flow filter 18 separates the second quantity 41 of the process fluid 42 into the second quantity 59 of the permeate fluid 60 and the second quantity 74 of the retentate fluid 73 as represented by the step 102. Specifically, the first quantity 39 of the process fluid 42 is passed tangentially across the first tangential flow filter 16 at a positive pressure relative to a permeate side of the first tangential flow filter 16. The control unit 90 operates the permeate pump 52, opens the first permeate flow control valve 54, and closes the second permeate flow control valve 56 to feed the first quantity 58 of the permeate fluid 60 to the permeate collection unit 44 via the first permeate flow path 46 and the second permeate flow path 48. Further, the control unit 90 closes the first retentate flow control valve 70 and opens the second retentate flow control valve 72 to feed the second quantity 74 of the retentate fluid 73 through the second branch portion 68 and the main portion 64 of the retentate flow path 62 to the bioreactor 12.

In accordance with the embodiments of the present specification, the control unit 90 enables to monitor a plurality of process parameters discussed herein above for determination of the clogging or the substantial clogging of the first tangential flow filter 16. Thereby, it is possible to divert the flow of the process fluid 42 through the second tangential flow filter 18. Hence, it is possible to prolong the duration of the perfusion process for a longer period of time.

While only certain features of the specification have been illustrated and described herein, many modifications and changes will occur to those skilled in the art. It is, therefore, to be understood that the appended claims are intended to cover all such modifications and changes as fall within the true spirit of the specification.

The invention described above, and illustrated provides one example of the invention, whereas in practice other examples would be apparent to the skilled addressee. In addition modifications which would readily occur to the skilled address include the provision of more than two filters. For example three, four or more filters could be provided, together with the controller which determines the performance of each filter used, and sequentially switches flow in the same manner as flow is controlled for the first and second filters mentioned above.

The invention claimed is:

1. A method for automatic operation of a perfusion bioprocessing system, the method comprising steps of:
   inducing a first quantity of a process fluid for a cell culture to flow from a bioreactor to a first tangential flow filter via a recirculation flow path;
   operating a control unit to control at least one first feed flow control device in the recirculation flow path for controlling the flow of the first quantity of the process fluid;
   allowing the first tangential flow filter to separate the first quantity of the process fluid into a first quantity of a permeate fluid and a first quantity of a retentate fluid;
   inducing a second quantity of the process fluid to flow from the bioreactor to a second tangential flow filter via the recirculation flow path, automatically bypassing the first tangential flow filter upon determination of a clogged or a substantially clogged condition of the first tangential flow filter by the control unit;
   operating the control unit to control at least one of the at least one first feed flow control device and at least one second feed control device in the recirculation flow path for controlling the flow of the second quantity of the process fluid; and allowing the second tangential flow filter to separate the second quantity of the process fluid into a second quantity of the permeate fluid and a second quantity of the retentate fluid;

wherein the recirculation flow path is configured to recirculate the process fluid from the bioreactor, through one or both of the first tangential flow filter and the second tangential flow filter, back to the bioreactor; and wherein the first tangential flow filter and the second tangential flow filter are arranged in series.

2. The method as claimed in claim 1, comprising determining a flow rate of the first quantity of the permeate fluid in a permeate flow path by a permeate flow sensor.

3. The method as claimed in claim 2, wherein operating the control unit comprises steps of:
determining a permeate flux rate of the first tangential flow filter based on the determined flow rate of the first quantity of the permeate fluid; and
determining the clogged or the substantially clogged condition of the first tangential flow filter based on the determined permeate flux rate of the first tangential flow filter.

4. The method as claimed in claim 3, wherein operating the control unit comprises a step of determining the clogged or the substantially clogged condition of the first tangential flow filter if the determined permeate flux rate is less than a threshold permeate flux rate.

5. The method as claimed in claim 3, wherein operating the control unit comprises steps of:
determining a change in rpm of a permeate pump in the permeate flow path based on at least one of the flow rate of the first quantity of the permeate fluid and determined revolutions per minute of the permeate pump; and
determining the clogged or the substantially clogged condition of the first tangential flow filter based on the determined change in rpm of the permeate pump.

6. The method as claimed in claim 5, wherein operating the control unit comprises a step of determining the clogged or the substantially clogged condition of the first tangential flow filter if the determined permeate flux rate is less than a threshold permeate flux rate.

7. The method as claimed in claim 1, comprising determining a pressure of the first quantity of the permeate fluid in a permeate flow path by a permeate pressure sensor; wherein operating the control unit further comprises determining the clogged or the substantially clogged condition of the first tangential flow filter based on the determined pressure of the first quantity of the permeate fluid.

8. The method as claimed in claim 7, wherein operating the control unit comprises a step of determining the clogged or the substantially clogged condition of the first tangential flow filter if the determined pressure of the first quantity of the permeate fluid is less than a threshold pressure.

9. The method as claimed in claim 1, comprising determining a rpm of a recirculation pump in the recirculation flow path by the control unit; wherein operating the control unit further comprises determining the clogged or the substantially clogged condition of the first tangential flow filter based on the determined rpm of the recirculation pump.

10. The method as claimed in claim 9, wherein operating the control unit comprises a step of determining the clogged or the substantially clogged condition of the first tangential flow filter if the determined rpm of the recirculation pump is greater than a threshold rpm.

11. The method as claimed in claim 1, comprising:
determining a pressure of the first quantity of the process fluid; and
determining a pressure of the first quantity of the retentate fluid;
wherein operating the control unit further comprises determining the clogged or the substantially clogged condition of the first tangential flow filter based on the determined pressure of the first quantity of the process fluid and the determined pressure of the first quantity of the retentate fluid.

12. The method as claimed in claim 11, wherein operating the control unit comprises a step of determining the clogged or the substantially clogged condition of the first tangential flow filter if a pressure difference across the first tangential flow filter is greater than a threshold pressure.

13. The method as claimed in claim 1, comprising:
determining a pressure of the first quantity of the process fluid;
determining a pressure of the first quantity of the retentate fluid; and
determining a pressure of the first quantity of the permeate fluid; wherein operating the control unit comprises steps of:
determining a transmembrane pressure based on the pressure of the first quantity of the process fluid, the pressure of the first quantity of the permeate fluid, and the pressure of the first quantity of the retentate fluid; and
determining the clogged or the substantially clogged condition of the first tangential flow filter based on the determined transmembrane pressure.

14. The method as claimed in claim 13, wherein operating the control unit comprises a step of determining the clogged or the substantially clogged condition of the first tangential flow filter if the determined transmembrane pressure is greater than a threshold pressure.

15. The method as claimed in claim 14, wherein operating the control unit comprises a step of determining the threshold pressure based on a plurality of parameters comprising a determined flow rate of the first quantity of the permeate fluid in a permeate flow path, cell viability within the permeate fluid, cell density within the permeate fluid, and a determined permeate flux rate of the first tangential flow filter.

16. The method as claimed in claim 1, further including:
providing one or more additional tangential flow filters
inducing a further flow of an additional process fluid to flow from an additional bioreactor to said one or more additional filters; operating an additional control unit to control at least one additional first feed flow control device in the recirculation flow path for controlling the further flow of the process fluid;
allowing the one or more additional filters to separate the first quantity of the process fluid into an additional quantity of a permeate fluid and an additional quantity of a retentate fluid; and
inducing a yet further quantity of the process fluid to flow from the additional bioreactor to the additional filter via the recirculation flow path, bypassing the first, second and any additional tangential flow filters, upon determination of a clogged or a substantially clogged condition of the first, second or any additional tangential flow filters.

17. An automatic perfusion bioprocessing system comprising:
- a bioreactor;
- a recirculation flow path provided with at least one first feed flow control device and at least one second feed control device;
- a first tangential flow filter coupled to the bioreactor via the recirculation flow path;
- a second tangential flow filter coupled to the bioreactor via the recirculation flow path;
- a permeate flow path, wherein the first tangential flow filter and the second tangential flow filter are coupled to the permeate flow path;
- a retentate flow path, wherein the first tangential flow filter and the second tangential flow filter are coupled to the retentate flow path; and
- a control unit coupled to the at least one first feed flow control device and the at least one second feed control device;
- wherein the control unit is configured to control the at least one first feed flow control device for controlling a flow of a first quantity of a process fluid from the bioreactor to the first tangential flow filter via the recirculation flow path;
- wherein the control unit is further configured to control at least one of the at least one first feed flow control device and the at least one second feed control device for controlling a flow of a second quantity of the process fluid from the bioreactor to the second tangential flow filter via the recirculation flow path, automatically bypassing the
- first tangential flow filter upon determination of a clogged condition or a substantially clogged condition of the first tangential flow filter;
- wherein the recirculation flow path is configured to recirculate the process fluid from the bioreactor, through one or both of the first tangential flow filter and the second tangential flow filter, back to the bioreactor; and
- wherein the first tangential flow filter and the second tangential flow filter are arranged in series.

18. The perfusion bioprocessing system as claimed in claim 17, comprising a permeate flow sensor coupled to the permeate flow path, wherein the control unit is communicatively coupled to the permeate flow sensor.

19. The perfusion bioprocessing system as claimed in claim 17, comprising:
- a feed pressure sensor coupled to the recirculation flow path;
- a retentate pressure sensor coupled to the retentate flow path; and
- a permeate pressure sensor coupled to the permeate flow path;
- wherein the control unit is communicatively coupled to the feed, retentate, and permeate pressure sensors.

20. The perfusion bioprocessing system as claimed in claim 17, wherein the recirculation flow path comprises a main portion, a first branch portion, and a second branch portion, wherein the bioreactor is coupled to the first tangential flow filter via the main portion and the first branch portion, and wherein the bioreactor is coupled to the second tangential flow filter via the main portion and the second branch portion.

21. The perfusion bioprocessing system as claimed in claim 17, wherein the permeate flow path comprises a first permeate flow path and a second permeate flow path, and wherein the first tangential flow filter is coupled to a permeate collection unit via the first permeate flow path and the second permeate flow path.

22. The perfusion bioprocessing system as claimed in claim 21, wherein the second tangential flow filter is coupled to the permeate collection unit via the second permeate flow path.

23. The perfusion bioprocessing system as claimed in claim 17, wherein the retentate flow path comprises a main portion, a first branch portion, and a second branch portion, wherein the bioreactor is coupled to the first tangential flow filter via the main portion and the first branch portion, and wherein the bioreactor is coupled to the second tangential flow filter via the main portion and the second branch portion.

24. The perfusion bioprocessing system as claimed in claim 17, further comprising one or more additional tangential flow filters, the control unit being further arranged to cause sequential filtering of fluids through the one or more additional tangential flow filters following the determination of a clogged or substantially clogged condition of the first and second filters.

* * * * *